United States Patent [19]

Mitchell

[11] 4,026,880

[45] May 31, 1977

[54] SILANES HAVING AN AMINE FUNCTIONAL GROUP THEREON

[75] Inventor: Tyrone D. Mitchell, Rensselaer, N.Y.

[73] Assignee: General Electric Company, Waterford, N.Y.

[22] Filed: Aug. 5, 1971

[21] Appl. No.: 169,481

[52] U.S. Cl. .............................. 260/239 E; 209/5; 260/239 A; 260/239 BF; 260/293.73; 260/293.78; 260/293.79; 260/293.82; 260/293.85; 260/293.87; 260/326.42; 260/326.43; 260/448.8 R

[51] Int. Cl.² ....................................... C07D 203/10

[58] Field of Search ..... 260/239 E, 239 A, 239 BF, 260/293.73, 293.78, 293.79, 293.82, 293.85, 293.87, 293.88, 326.42, 326.43, 448.8 R

[56] References Cited

UNITED STATES PATENTS 3,243,429  3/1966  Ham ............... 260/239 E

FOREIGN PATENTS OR APPLICATIONS 1,163,818  9/1964  Germany

Primary Examiner—Raymond V. Rush
Attorney, Agent, or Firm—Donald J. Voss; E. Philip Koltos; Frank L. Neuhauser

[57] ABSTRACT

A silicone compound of the formula,

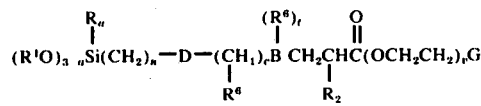

where R, $R^1$, $R^2$ and $R^6$ are hydrocarbon radicals, B is selected from nitrogen, oxygen and sulfur, D is selected from a divalent hydrocarbon radical or oxygen, G is selected from various nitrogen radicals, and $a$, $n$, $t$, $c$ and $v$ are whole numbers. The above compound is eminently useful as a flocculent for colloidal biological wastes, as well as being useful as a glass sizing agent.

3 Claims, No Drawings

SILANES HAVING AN AMINE FUNCTIONAL GROUP THEREON

BACKGROUND OF THE INVENTION

The present invention relates to a silicone compound and, in particular, the present invention relates to a silicone compound having an amine functional group thereon.

Flocculents have been used in the past and in the present time and in various types of processes for coagulating precipitating colloidal material. As is known at the present time, there has been an emphasis in sewage disposal and sewage purification. In such sewage disposal and water purification systems there are suspended in the water system colloidal particles of biological wastes or colloidal particles of organic matter which have precipitated in the best by various flocculents.

Substances having activity as flocculents fall into four main classes such as, for instance, the colloidal hydroxides of polyvalent metal ions and water-soluble polymers of the anionic, non-anionic, and cationic polyelectrolyte classes. Although inorganic materials such as silica sol is a flocculent for some types of systems, it has been found that it is not very efficient with organic wastes. On the other hand, cationic polyelectrolytes were found to be substantially more efficient than the metal hydroxides as flocculents for organic waste.

There are several theories as to the manner and way in which the different types of flocculents operate. One such theory is that flocculents operate as efficiently in a particular system such as an organic waste system, as the flocculents are in distributing or removing the electrical charges from the colloidal particles.

In addition, there is a constant search for efficient bonding or sizing agents for bonding different types of organic resins to glass and glass fibers, as well as other types of glass material. It is well known the wide spread use of glass fibers in the fabrication of various types of manufactured items and it can be appreciated the desire to obtain glass sizing agents that will bond normally unreactive type of resins to glass fiber. One such type of unreactive resins which are difficult to bond to glass fibers is resins containing anhydrides.

Accordingly, it is one object of the present invention to provide a novel class of silicone compounds having an amine-functional group thereon.

It is another object of the present invention to provide a process for producing a novel class of silicone compounds having a novel type of amine-functional group thereon.

It is yet another object of the present invention to provide a new class of silicone compounds which are very efficient flocculating agents for colloidal organic matter.

It is yet an additional object of the present invention to provide a novel class of silicone compounds for bonding unusually unreactive resins to glass fibers and glass types of material.

These and other objects of the present invention are accomplished by means of the objects below.

SUMMARY OF THE INVENTION

In accordance with the present invention, there is provided a novel class of silicone compounds having the formula,

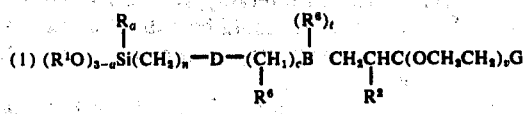

where R and $R^1$ are selected from the class consisting of monovalent hydrocarbon radicals and halogenated monovalent hydrocarbon radicals, $R^2$ and $R^6$ are selected from the class consisting of hydrogen, alkyl and aryl radicals of up to 10 carbon atoms, B is selected from the class consisting of nitrogen, oxygen and sulfur, G is selected from the class consisting of

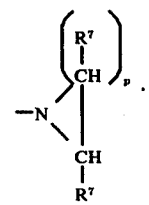

and $-N(R^7)_2$, where $R^7$ is selected from the class consisting of hydrogen and alkyl radicals of up to 8 carbon atoms, D is selected from the group consisting of

and 0, n is a whole number from 1 to 10, c is a whole number from 1 to 10, t is a whole number that varies from 0 to 1, v is a whole number that varies from 1 to 5 p is a whole number that varies from 1 to 6 and a is a whole number that varies from 0 to 2.

In the above formula, preferably a is equal to 0. Furthermore, preferably $R^1$ is methyl, $R^2$ is methyl and $R^6$ is hydrogen. The preferred compound coming within the scope of claim 1, is:

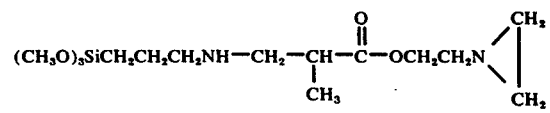

DETAILED DESCRIPTION OF THE PREFERRED EMBODIMENT

In formula (1) defining compounds within the present invention, R and $R^1$ are monovalent hydrocarbon radicals, and substituted monovalent hydrocarbon radicals, for example, alkyl radicals, e.g., methyl, ethyl, propyl, butyl, octyl, etc. radicals; aryl radicals, e.g., phenyl, naphthyl, tolyl, xylyl, etc. radicals; aralkyl radicals, e.g., benzyl, phenylethyl, etc. radicals; alkenyl radicals, e.g., vinyl, allyl, cyclohexenyl, etc. radicals; cycloalkyl radicals, e.g., cycloheptyl, etc. radicals; halogen-substituted monovalent hydrocarbon radicals such as, for example, chloromethyl, chloroethyl, dibromophenyl, etc. radicals; as well as other such types of radicals. If a is not 0, it is preferably that R is methyl. Insofar as $R^1$ is concerned, it is preferable that this radical be ethyl or methyl but, however, it is preferably any type of alkyl radical of up to 10 carbon atoms. The radicals $R^2$ and $R^6$ are preferably selected from hydrogen, alkyl and aryl radicals of up to 10 carbon atoms. The radicals $R^2$ and $R^6$ may also be halogen-substituted alkyl and aryl radicals. Preferably, $R^2$ is a methyl radical and $R^6$ is hydrogen. It should be noted that each $R^6$ radical in formula (1) may vary independently from the other $R^6$ radical.

In the above formula, B is selected from the class consisting of nitrogen, sulfur and oxygen and the radical D is a divalent radical which is selected from $CH_2$, that is, methylene and oxygen. In addition, in formula (1), $R^7$ may be selected from hydrogen, alkyl radicals or aryl radicals of up to 10 carbon atoms. More preferably, $R^7$ is an alkyl radical of up to 10 carbon atoms and, more usually, methyl, ethyl, propyl. In the above formula (1), $n$ is a whole number that varies from 1 to 10, $c$ is a whole number that varies from 1 to 10, $v$ is a whole number that varies from 1 to 5 and the most preferred values for $n$, $c$ and $v$ is 1, 1 and 1, respectively. In the case of $t$, this letter which may vary from 0 to 1 must be 0 when B is equal to either oxygen or sulfur. In the case of $p$, it is a whole number that varies from 1 to 6 and preferably 1.

The compounds coming within the scope of formula (1) and which are preferred in the present case are as follows:

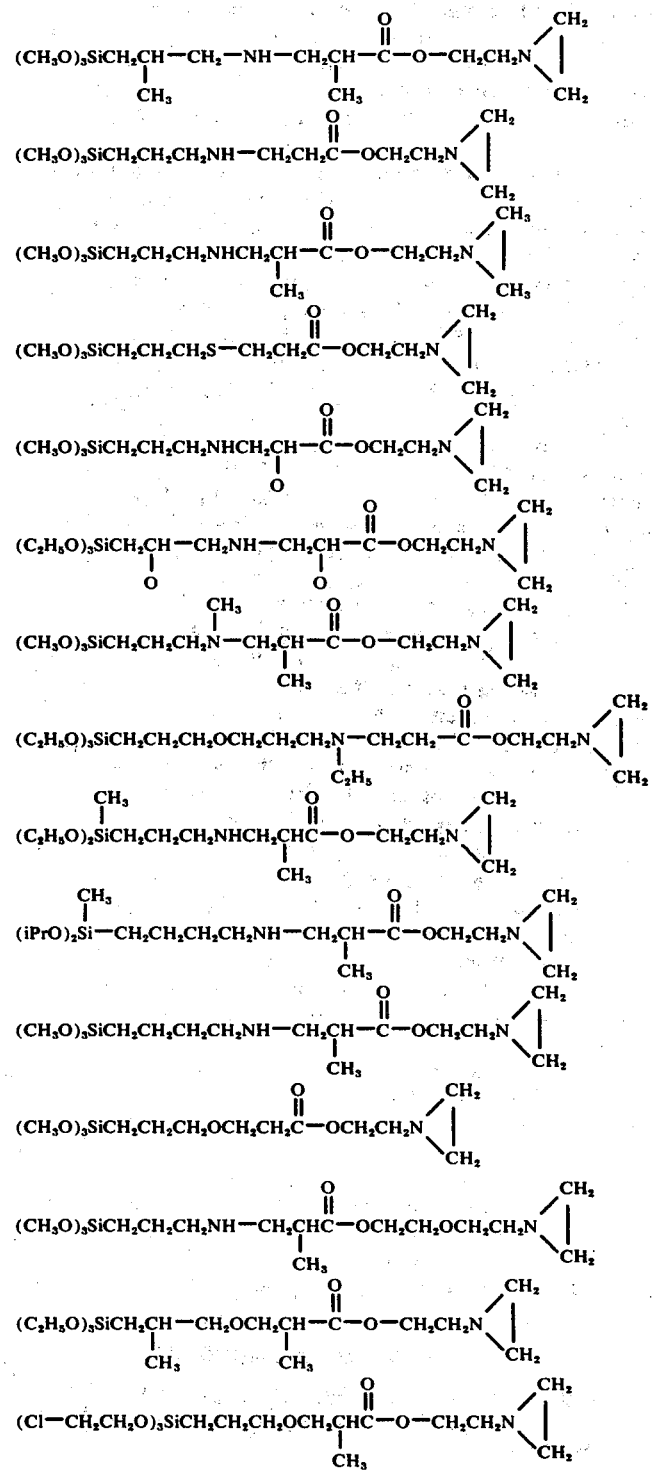

-continued

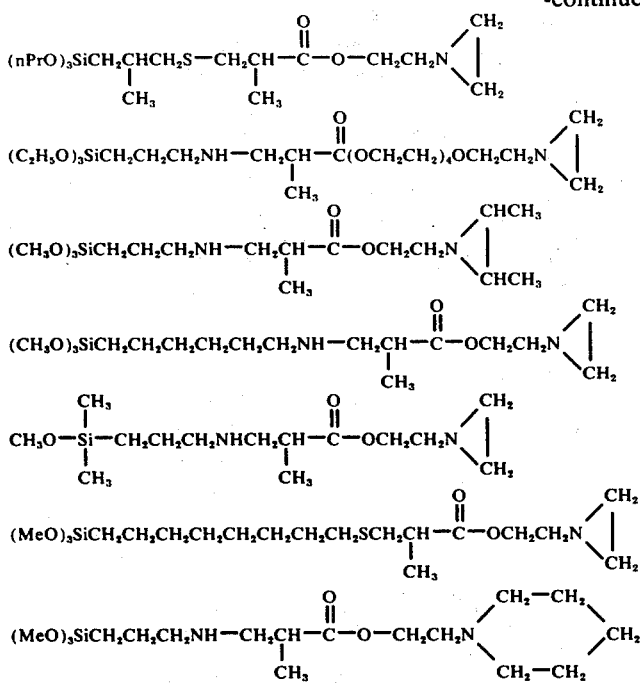

The compound of the present invention is produced by reacting a compound of the formula,

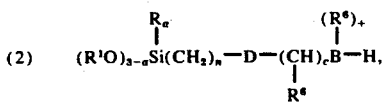

with a compound of the formula,

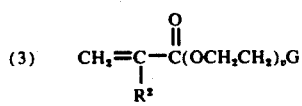

where R, $R^1$, $R^2$, $R^6$, B, D, and G are as defined previously. Compounds of formula (3) above are well known in the art and are sold by Alcolac Chemical Company, Baltimore, Md.

In the above reaction, it is preferable that the compounds of formulas (2) and (3) be reacted in stoichiometric proportions. This is for the reason of obtaining an efficient reaction. Although either reactant may be used in excess, this has not been found to be necessary and the reaction is best carried forward by keeping the reactants in a stoichiometric relationship. The reaction may be carried out either in the presence of a base or acid catalyst, although a catalyst is not necessary. A catalyst is preferred and specifically a basic catalyst is preferred in that the reaction proceeds faster and, furthermore, a higher yield is obtained. Examples of acid catalysts that may be used in the present reaction are ammonium chloride, toluene sulfonic acid and other types of Lewis acid catalysts. Although an acid catalyst may be used, it is not preferred since it may coreact with the G radical in the compound of formula (3).

A basic catalyst is preferred, such as sodium hydroxide, sodium methoxide, potassium hydroxide, etc. Of these catalysts, of course, the most preferable are the sodium methoxides and ethoxides. Such a catalyst is used in a concentration of 0.5 to 5% by weight of the reaction mixture, although a concentration of the catalyst of about 0.5 to 1.5% by weight of the reaction mixture is desirable.

In this reaction there may be utilized a solvent, although such a solvent is not necessary. Examples of the solvents that may be used in the present reaction are the common types of inert hydrocarbon solvents, such as, for example, xylene, toluene, mineral spirits, naphthylene, benzene, etc.

The reaction can be carried out at room temperature. However, for most practical purposes, it is desired to heat the reaction mixture to a temperature within the range of 60° to 120° C for a period of time varying anywhere from 5 to 24 hours. As pointed out previously, a catalyst or a high reaction temperature condition is not necessary. Such catalyst and higher reaction temperature conditions are preferred if the reaction is to obtain a high yield within 24 hours. Thus, under the above preferred conditions, there is obtained at least 65% yield of the product of formula (1) by reacting compounds of formula (2) and formula (3) under the preferred conditions. If, however, the mixture is maintained at the preferred reaction conditions for periods of time varying from 36 hours to 48 hours and more, there may be obtained a yield of the desired compound of formula (1) as high as 90 to 95%.

In the above reaction, it is desired that the reaction be maintained anhydrous since water will possibly attack the $R^1O$ group attached to the silicon in the compound of formula (2). Further, the compound of formula (3) is a very reactive compound which can be caused to polymerize with itself by impurities or other types of material in the reaction chamber. So, for instance, traces of acids, bases, as well as salts in the reaction chamber, will cause the compound of formula (3) to polymerize with itself rather than reacting with the compound of formula (2). As a result, it is necessary to keep the reaction chamber extremely clean. Further, in order to combat such possible amounts of traces of impurities, an inhibitor is used in the reaction.

Examples of such inhibitors which may be used are hydroquinone and dimethoxy benzene. Such inhibitors are preferably used in the reaction in a concentration of 0.1 to 2% by weight of the reaction mixture. Further, in spite of the inhibitor and the use of a clean reaction chamber, the compound of formula (3) may polymerize with itself if more than the necessary amount of basic or acid catalyst is used in the reaction. Thus, for these purposes, it is desired that the acid and preferably basic catalyst be no more than 5% by weight of the reaction mixture and, more perferably, no more than 2% by weight of the reaction mixture.

The compound of formula (2) may be obtained by reacting a compound of the formula, (4)   $(Z)_{3-a}SiH\overset{R_a}{|}$ , with a compound of the formula, (5)   $CH_2=CH(CH_2)_e-D_k-(CH)_fCN\overset{}{\underset{R^6}{|}}$ , where Z is halogen, D is as defined previously, $e$ is equal to from 0 to 8, D is equal to $\overset{CH}{\underset{R^6}{|}}$ or oxygen, $e$ is a whole number that varies from 0 to 8, $k$ varies from 0 to 1 and $f$ varies from 0 to 10 and $R^6$ is as previously defined.

The compounds of formulas (4) and (5) are reacted in the presence of the catalyst system defined in Bluestein U.S. Pat. No. 2,971,970. The disclosure of that patent is incorporated into this case by reference. A preferred catalyst as suggested in the above patent is the combination of triethylamine cuprous chloride and tetramethylethylene-diamine. The reaction is preferably carried out stoichiometrically and no solvent is necessary. However, one of the usual inert hydrocarbon solvents may be used in the system. The reaction may be carried out in the temperature range of 50° to 100° C but is preferably carried out in a temperature of 60° to 80° C.

The reaction of compounds of formulas (4) and (5) must be carried out anhydrously since water will poison the catalyst system. With this catalyst, and in the preferred temperature range, if the reaction is allowed to proceed from 1 to 6 hours, there is obtained anywhere from 60 to 70 yield of the desired nitrile product. The halogen groups on the resulting silane nitrile product may then be alkoxylated by reacting the silane-nitrile product with an alcohol such as $R^1OH$, where $R^1$ is as previously defined.

The catalyst system illustrated in the Bluestein patent is useful in the cases where $e$, $k$, and $f$ are equal to 0. In the cases where $e$, $k$ and $f$ are equal to values other than 0, then the reaction of the SiH-olefin addition reaction between the compound of formula (4) and the compound of formula (5) must take place in the presence of a platinum catalyst.

The platinum compound catalyst can be selected from the group of platinum compound catalysts which are operative to catalyze the addition of silicon hydrogen bonds across olefinic bonds. Among the many useful catalysts for this addition reaction are chloroplatinic acid as described in U.S. Pat. No. 2,823,218 — Speier et al, the reaction product of chloroplatinic acid with either an alcohol and ether or an aldehyde as described in U.S. Pat. No. 3,220,972 — Lamoreaux, trimethylplatinum iodide and hexamethyldi—platinum as described in U.S. Pat. No. 3,313,773 — Lamoreaux, the platinum olefin complex catalyst as described in U.S. Pat. No. 3,159,601 — Ashby, and the platinum cyclopropane complex catalyst described in U.S. Pat. No. 3,159,662 — Ashby.

The SiH-olefin addition reaction may be run at room temperatures of temperatures up to 200° C, depending upon the catalyst concentration. The catalyst concentration can vary from $10^{-7}$ to $10^{-3}$ and preferably $10^{-5}$ to $10^{-4}$ mole of platinum as metal, per mole of the olefinic containing molecules present. In this platinum catalyzed reaction preferably the compounds of formula (4) and (5) are reacted in stoichiometric proportions. Additionally, it is preferable a solvent, one of the common inert hydrocarbon solvents, be used.

The addition product of the reaction of compounds of formulas (4) and (5) is reacted with the alcohol preferably at reflux conditions, such as in the temperature range of 50° to 120° C. If the reaction temperature is maintained at the lower end of the temperature range, then it is desirable to apply vacuum to the reaction chamber so as to remove the hydrogen chloride that is formed by the vacuum, otherwise the hydrogen chloride will attack the nitrile group in the silane compound.

Another way of removing the HCl that is formed in the alcoholysis is to carry out the reaction in a solvent in which hydrogen chloride is not soluble. Such a solvent is xylene, toluene, methylorthoformate.

After the alcoholysis, the nitrile group on the silane may be hydrogenated so as to change the nitrile group to a hydrocarbon amine group. This is done by reacting the product of the alcoholysis reaction with hydrogen in the oresence of a nickel catalyst. Such a process is disclosed in U.S. Pat. No. 2,930,809, whose disclosure is incorporated into the present case by reference. As preferred, the hydrogenation reaction is carried out by mixing the silane with the nitrile group thereon with hydrogen gas and heating the resultant mixture to 80° to 140° C in the presence of a Raney nickel catalyst. The reaction may be carried out under pressure or not. If pressure is used, it is preferable that the pressure vessel be maintained anywhere from 20 to 80 psig.

Using the above method and disclosure, it is possible to obtain a compound within the scope of formula (3). Such compounds within formula (3) where B is equal to nitrogen, as disclosed by the above process, are sold by the General Electric Company, Waterford, N.Y., the present assignee. In the case where B is sulfur, such a compound is disclosed in German Pat. No. 1,163,818. Such compounds where B is equal to sulfur, is sold by Union Carbide Corporation.

The above is a general description of the present invention. The examples below are given for the purpose of illustration and are not intended in any way to limit the invention as claimed.

EXAMPLE 1

This experiment illustrates the method for making 2-(1-aziridinyl)ethyl 2-methyl-3- [3-(trimethoxysilyl) propylamino] propionate of the formula,

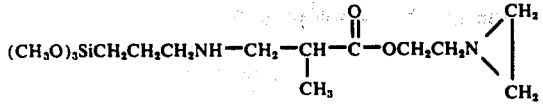

A mixture of 895 grams (5.0 moles) of 2-aminopropyltrimethoxysilane, 775 grams (5.0 moles) of 2-(1-aziridinyl)-ethyl methacrylate, 1.69 grams of trimethylchlorosilane and 1.56 grams of Ethyl 703 inhibitor is placed in a 3,000 ml flask equipped with a thermometer, an air driven stirrer and a reflux condenser. The mixture is placed under an atmosphere of dry nitrogen and heated at 100° C while agitating for 24 hours. At the end of the heating period, the reaction mixture is equipped for vacuum distillation and all volatile materials are distilled up to a pot temperature of 150° C at 1.0 mm pressure. Then 425 grams of unreacted starting materials are recovered from the flash distillation. The residue is weighed and filtered through Celite. The 1176 grams of product is obtained at a yield of 70%. Analysis by nuclear magnetic resonance, infrared and percent nitrogen confirmed the above structure.

EXAMPLE 2

This experiment illustrates the method for making 2-(1-aziridinyl)ethyl 2-methyl-3- [3-(trimethoxysilyl)propyl-thio] propionate of the formula,

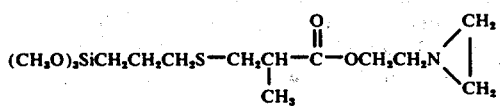

A mixture of 40 grams (0.20 mole) of 3-mercaptopropyltrimethoxysilane and 31 grams (0.20 mole) of 2-(1-aziridinyl)-ethylmethacrylate is placed in a 100 cc three-necked flask equipped with a thermometer, an air driven stirrer and a reflux condenser. The 3-mercaptopropyltrimethoxysilane is synthesized by reacting 3-chloropropyltrimethoxysilane with sodium hydrosulfide in dimethylformamide. The 3-chloropropyltrimethoxysilane is synthesized from trichlorosilane and allyl chloride in the presence of a platinum catalyst followed by reaction with an alcohol to produce the trialkoxy derivative. The mixture is placed under an atmosphere of dry nitrogen and heated at 100° C while agitating for 24 hours. At the end of the heating period, the reaction mixture is equipped for vacuum distillation and all volatile materials are distilled up to a pot temperature of 150° C at a pressure of 1.0 millimeter. Eleven grams of unreacted starting material are recovered from the flash distillation. The residue is weighed and filtered through Celite. The 59 grams of product is obtained at a yield of 84%. Analysis by nuclear magnetic resonance and infrared spectroscopy confirmed the structure.

EXAMPLE 3

This experiment illustrates a method by which 2-(1-aziridinyl)ethyl 2-methyl-3- [3-(triethoxysilyl)-propoxy] propionate is made. The formula is,

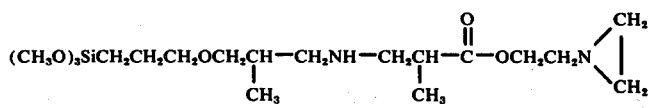

While this mixture is agitating and being heated to 50° C, in a 100 cc three-necked flask equipped with a dropping funnel, a thermometer, a magnetic bar for stirring, and a reflux condenser is placed 444 grams (0.20 mole) of 3-hydroxypropyltriethoxysilane and 0.4 grams of anhydrous sodium ethoxide. The compound (3-hydroxypropyltriethoxysilane is prepared by reacting allyl alcohol with trimethylchlorosilane to make the allyloxy trimethylsilane. To this is added triethoxysilane in the presence of a platinum hydrosilation catalyst. After purification of the product, triethoxysilylpropoxytrimethylsilane, the desired product is generated by reacting this with a large excess of ethanol using sodium ethoxide catalyst and continuously distilling trimethylethoxysilane from the reaction mixture. The compound 3-hydroxypropyltriethoxysilane is obtained from the last step in 80% yield.) 62.0 grams (0.40 mole) of 2-(1-aziridinyl)ethylmethacrylate is placed in the dropping funnel with 0.07 gram of Ethyl 703 inhibitor. The temperature is kept at 50° C to prevent transalkoxylation or cyclicization involving the hydroxypropyl group and the ethoxy groups on silicon which usually occurs at higher temperatures. The material in the dropping funnel is added dropwise to the material in the reaction flask. At the end of the addition the mixture is heated at 50° C until analysis by gas chromatography show the 3-hydroxypropyltriethoxysilane to be completely consumed or from 12–24 hours. At the end of the reaction, the reaction mixture is filtered after cooling to remove insoluble sodium ethoxide and the excess aziridinylethyl methacrylate is distilled away from the product under vacuum. The residue is collected and identified by nuclear magnetic resonance and infrared spectroscopy and by percent nitrogen analysis.

EXAMPLE 4

In this experiment the synthesis of 2-(aziridinyl) ethyl 2-methyl-3-{3- [3-(trimethoxysilyl)propoxy] 2-methylpropylamino}propionate is illustrated. The formula is, $$(CH_3O)_3SiCH_2CH_2CH_2OCH_2CH-CH_2NH-CH_2CH-C-OCH_2CH_2N\begin{matrix}CH_2\\ |\\ CH_2\end{matrix}$$
$$\quad\quad\quad\quad\quad\quad\quad\quad\quad\quad\quad\quad CH_3\quad\quad\quad CH_3\quad\quad O$$

In a 250 cc three-necked flask is added 116 grams (0.75 mole) of 2-(1-aziridinyl)ethyl methacrylate, 0.13 gram of ethyl 703 inhibitor, 124.5 grams (0.5 mole) of 3,3-amino-2-methylpropoxypropyl trimethoxysilane and 1.20 grams of anhydrous sodium methoxide. This mixture is heated at 80°-100° C for 24 hours. At the end of the heating period the reaction is processed by cooling and filtering to remove undissolved sodium methoxide, adding one gram of trimethylchlorosilane neutralizes the remaining catalyst dissolved in the reaction mixture. The reaction is distilled under vacuum to remove excess 2-(1-aziridinyl)ethyl methacrylate. It is distilled up to a temperature of 150° C at a pressure of 0.10 millimeter. The moderately viscous residue is collected and identified as the desired product by nuclear magnetic resonance and infrared spectroscopy and by analysis for percent nitrogen.

EXAMPLE 5

A compound within the scope of the present invention of the name, 2-{2-[2-(1-aziridinyl)ethoxy] ethoxy}ethyl 2-methyl-3-[3-(trimethoxysilyl)propylamino] propionate has the following structure,

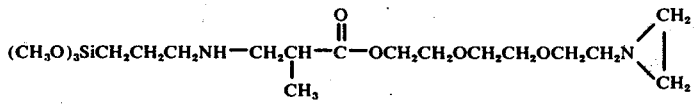

The synthesis of this compound comprises producing a mixture of 35.8 grams (0.20 mole) of 3-aminopropyltrimethoxysilane, 24.3 grams (0.10 mole) of 2{2-[2-(1-aziridinyl)ethoxy] ethoxy}ethyl methacrylate, 0.05 grams of hydroquinone inhibitor, and 0.3 grams of sodium methoxide which is agitated and heated at 80° C for 24 hours. At the end of the heating period the reaction mixture is cooled and filtered to remove undissolved sodium methoxide. The 0.6 grams of trimethylchlorosilane is added to neutralize and dissolve sodium methoxide. The reaction mixture is then distilled under vacuum to remove excess 3-aminopropyltrimethoxysilane. The residue remaining after distillation at 150° C and 0.10 millimeters is the desired product. It is identified by nuclear magnetic resonance and infrared spectroscopy and by analysis for percent nitrogen.

I claim:

1. A silicone compound of the formula,

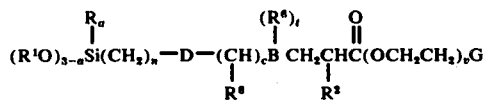

where R is selected from the class consisting of monovalent hydrocarbon radicals and halogenated monovalent hydrocarbon radicals and $R^1$ is an alkyl radical of up to 10 carbon atoms, $R^2$ and $R^6$ are selected from the class consisting of hydrogen, alkyl and aryl radicals of up to 10 carbon atoms, B is selected from the class consisting of nitrogen, sulfur and oxygen, D is selected from the group consisting of

and oxygen, G is selected from the class consisting of

and $N(R^7)_2$, where $R^7$ is selected from the class consisting of hydrogen and alkyl radicals of up to 10 carbon atoms, $n$ is a whole number from 1 to 10, $c$ is a whole number from 1 to 10, $v$ is a whole number that varies from 1 to 5, $p$ is a whole number that varies from 1 to 6, $t$ is a whole number that varies from 0 to 1 and $a$ is a whole number that varies from 0 to 2.

2. The silicone compound within the scope of claim 1, wherein R, $R^1$, $R^6$ and $R^2$ are methyl, $v$ is equal to 1, $n$ and $c$ are equal to 1 and D is

—CH—.
|
$R^6$

3. The silicone compound of claim 1 having the formula,

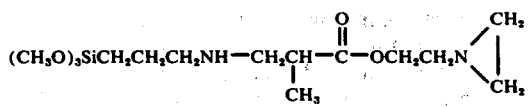

* * * * *